(12) United States Patent
Wu et al.

(10) Patent No.: US 8,155,263 B2
(45) Date of Patent: Apr. 10, 2012

(54) APPARATUS AND METHOD FOR VOLTAGE MODULATION IN X-RAY COMPUTED TOMOGRAPHY

(75) Inventors: Xiaoye Wu, Niskayuna, NY (US); David Allen Langan, Niskayuna, NY (US); James Walter LeBlanc, Niskayuna, NY (US); Dan Xu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 143 days.

(21) Appl. No.: 12/534,087

(22) Filed: Jul. 31, 2009

(65) Prior Publication Data

US 2011/0026668 A1 Feb. 3, 2011

(51) Int. Cl.
*H05G 1/60* (2006.01)
(52) U.S. Cl. .............................................. 378/4; 378/16
(58) Field of Classification Search ................ 378/4, 15, 378/19, 91, 92, 108, 115, 116
See application file for complete search history.

(56) References Cited

U.S. PATENT DOCUMENTS

| 5,001,735 | A | 3/1991 | Sammon |
| 5,485,494 | A | 1/1996 | Williams |
| 6,507,639 | B1 | 1/2003 | Popescu |
| 6,697,508 | B2 * | 2/2004 | Nelson .......................... 382/131 |
| 6,950,492 | B2 * | 9/2005 | Besson ............................. 378/5 |
| 7,086,780 | B2 | 8/2006 | Wu |
| 2005/0031082 | A1 | 2/2005 | Haaga |
| 2007/0140428 | A1 | 6/2007 | Toth |

FOREIGN PATENT DOCUMENTS

EP 1172069 A1 1/2002

* cited by examiner

*Primary Examiner* — Irakli Kiknadze
(74) *Attorney, Agent, or Firm* — Jason K. Klindtworth

(57) ABSTRACT

The present invention discloses a computed tomography imager comprising: an x-ray source disposed in a gantry; a detector assembly for receiving an x-ray emission from an x-ray source, the x-ray source and the detector assembly rotatable about an imaging target; an imager control system for selectively modulating a kVp operating value in the x-ray source during a scan slice in accordance with an x-ray modulation software program; and a computer for receiving data from the detector assembly, and for providing control signals to the imager control system by executing the x-ray modulation software program for at least a portion of the total possible rotational scanning range of the x-ray source.

16 Claims, 6 Drawing Sheets

APPARATUS AND METHOD FOR VOLTAGE MODULATION IN X-RAY COMPUTED TOMOGRAPHY

BACKGROUND OF THE INVENTION

The subject matter disclosed herein relates to computed tomography imaging systems and, more particularly, to an apparatus and method of x-ray voltage modulation for controlling patient exposure to radiation in such systems.

The imaging process in a computed tomography system utilizes an x-ray source and x-ray detectors to scan a patient, and to construct cross-sectional images of the patient from these scanned data. It is often desirable to limit the amount of patient exposure to x-ray radiation incurred during such scans. Referring to FIG. 1, a "third generation" computed tomography (CT) imaging system 10, for example, is configured to perform computed tomography imaging by means of photon counting and energy discrimination of x-rays at high flux rates. The CT imaging system 10 comprises a gantry 12, with a collimator assembly 18, a data acquisition system 32, and an x-ray source 14 disposed on the gantry 12 as shown. A support surface, such as a table 46, serves to move all or part of a target, such as a package (not shown) or a patient 22, through a gantry opening 48 in the gantry 12. During a scan to acquire x-ray projection data, the gantry 12 rotates about a center of rotation 24 along with the x-ray source 14 and the detector assembly 15.

Referring now also to FIG. 2, the x-ray source 14 projects a beam of x-rays 16 through the patient 22 onto a plurality of detector modules 20 in a detector assembly 12. The detector assembly 12 includes the collimator assembly 18, the detector modules 20, and the data acquisition system 32. Each detector module 20 in a conventional system produces an analog electrical signal that represents the intensity of an attenuated x-ray beam after it has passed through the patient 22. The data acquisition system 32 converts the sensed data to digital signals for subsequent processing. It can be appreciated that mage reconstruction for 3-D imaging requires a linear attenuation output. This may be achieved by initially performing a calibration at each of the kVp points of interest, typically using a water target, and can be a very time consuming operation.

Operation of the gantry 12 and the x-ray source 14 are controlled by a control mechanism 26. The control mechanism 26 includes an x-ray generator 28 that provides power and timing signals to the x-ray source 14, and a gantry motor controller 30 that controls the rotational speed and position (i.e., the gantry angle) of the moving components of the gantry 12. An image reconstruction processor 34 receives sampled and digitized x-ray data from the data acquisition system 32 and performs high speed reconstruction. Reconstructed images are applied as inputs to a computer 36 which can also store the images in a mass storage device 38.

The computer 36 also receives commands and scanning parameters input from an operator console 40. An associated display, such as a cathode ray tube display 42, allows an operator to observe the reconstructed image and other data from the computer 36. The commands and scanning parameters are used by the computer 36 to provide control signals and information to the data acquisition system 32, the x-ray generator 28, and the gantry motor controller 30. In addition, the computer 36 operates a table motor controller 44 which controls the motorized table 46.

Operating parameters for the x-ray source 14, such as peak x-ray tube kilovoltage (kVp) and x-ray tube current (mA), may be set from the operator console 40. To reduce patient dose, and to achieve improved image quality, the CT imaging system 10 may also have the capability of modulating the x-ray tube current during a scan. This modulation includes change to the x-ray tube current as the CT imaging system 10 scans at different height of the body, as well as x-ray tube current variation at the same patient height, but at different angular positions. The objective of x-ray tube current modulation is to deliver the optimal signal-to-noise ratio for each projection with improved patient dose management, such as by increasing x-ray tube current at longer mass penetration length. However, for a relatively fast scan speed, the operator may not be able to modulate the kVp to achieve the desired results, and the kVp may be left at a constant value. The prior art does disclose methods of modulating patient dose rate, such as exemplified in U.S. Pat. No. 6,233,310 "Exposure management and control system and method" and U.S. Pat. No. 7,545,915 "Dose rate control in an X-ray system," but such procedures do not provide the accuracy and the output linearity required for 3-D imaging.

While the use of x-ray tube current modulation can provide for patient x-ray radiation dose reduction and may yield better image quality (IQ), certain shortcomings have been identified with this method. The tube current modulation speed in conventional x-ray tubes, for example, is limited by the thermal constant of the tube cathode and cannot be varied as rapidly as the tube current modulation method may require. Also, because of the speed with which the x-ray source 14 rotates around the patient 22, the system operator can not manually modulate the x-ray tube output within an individual rotation but can provide some voltage modulation for limiting patient exposure only as successive rotations of the x-ray source 14 occur. This shortcoming may become a more severe problem with newer, even fast-rotating x-ray scanners. Moreover, increasing the x-ray tube current, such as may be required for relatively long mass penetration lengths, may result in a linear signal increase at the detector, indicating linear dose contribution. In addition, a "photon starvation" problem may result at the highest x-ray tube current capability of an imaging system, for a given x-ray tube voltage.

What is needed is a method of controlling x-ray radiation exposure in imaging systems which addresses the shortcomings of the prior art.

BRIEF DESCRIPTION OF THE INVENTION

In one aspect of the present invention, a computed tomography imager comprises: an x-ray source disposed in a gantry; a detector assembly for receiving an x-ray emission from the x-ray source, the x-ray source and the detector assembly rotatable about an imaging target; an imager control system for selectively modulating a kVp operating value in the x-ray source during a scan slice in accordance with an x-ray modulation software program; and a computer for receiving data from the detector assembly, and for providing control signals to the imager control system by executing the x-ray modulation software program for at least a portion of the total possible rotational scanning range of the x-ray source.

In another aspect of the present invention, a method for controlling patient exposure to radiation emitted in a scanning system gantry comprises: obtaining predetermined operating parameters as a function of gantry angle for modulating a kVp operating value for a radiation source during a scan; and modulating the kVp operating value for the radiation source during at least a portion of a scan slice in accordance with the operating parameters.

In yet another aspect of the present invention, a method for controlling patient exposure to radiation in a computed tomography scanning system comprises: irradiating the patient with an x-ray source controlled by an imager control system, the imager control system functioning to selectively modulating a kVp operating value for the x-ray source in accordance with an x-ray modulation software program; and modulating the kVp operating value during each scan slice of a computed tomography scan.

Other devices and/or methods according to the disclosed embodiments will become or are apparent to one with skill in the art upon review of the following drawings and detailed description. It is intended that all such additional devices and methods are within the scope of the present invention, and are protected by the accompanying claims.

DETAILED DESCRIPTION OF THE INVENTION

The invention includes a method of performing x-ray voltage modulation (hereinafter kVp modulation) for patient dose reduction to address the shortcomings of the prior art method of x-ray current modulation (hereinafter mA modulation). Patient adaptive scanning is achieved by means of modulating tube kVp, which action can also be accompanied by a change in mA. As kVp modulation can be very fast, typical a few orders of magnitude faster than that of mA modulation, kVp modulation can be readily implemented for fast-rotating scanners that may be developed in the future. Other advantages of using kVp modulation, rather than using only mA modulation, include: incurring less patient radiation dosage at long penetration view angles, and the ability to provide maximum radiation dosage as needed to preclude "photon starvation." In particular, increasing kVp results in a non-linear signal increase at the detector, due to both increase x-ray production (at constant mA) and better x-ray penetration at the higher kVp, resulting in less patient dose at long penetration view angles, for example.

Figure 1:
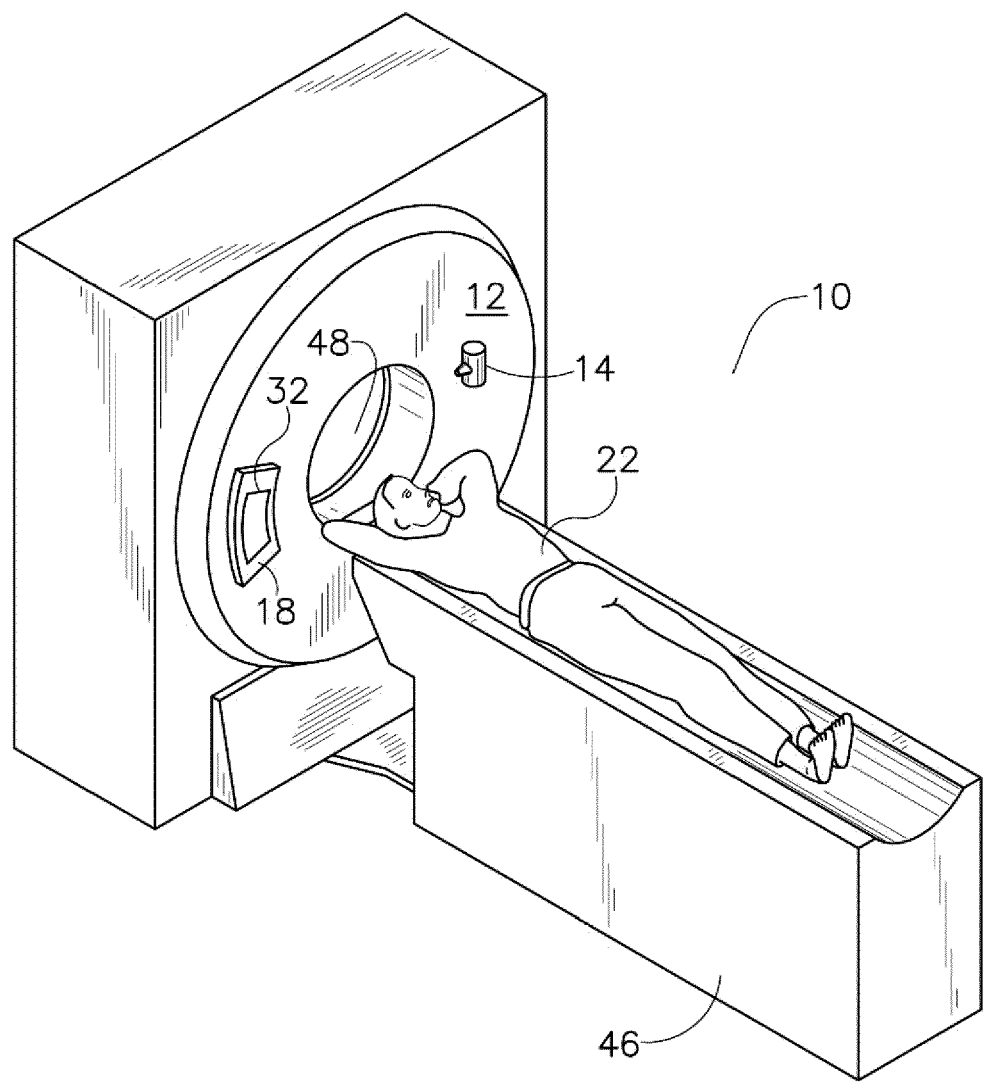
FIG. 1 shows a computed tomography imaging system, in accordance with the prior art.
Figure 2:
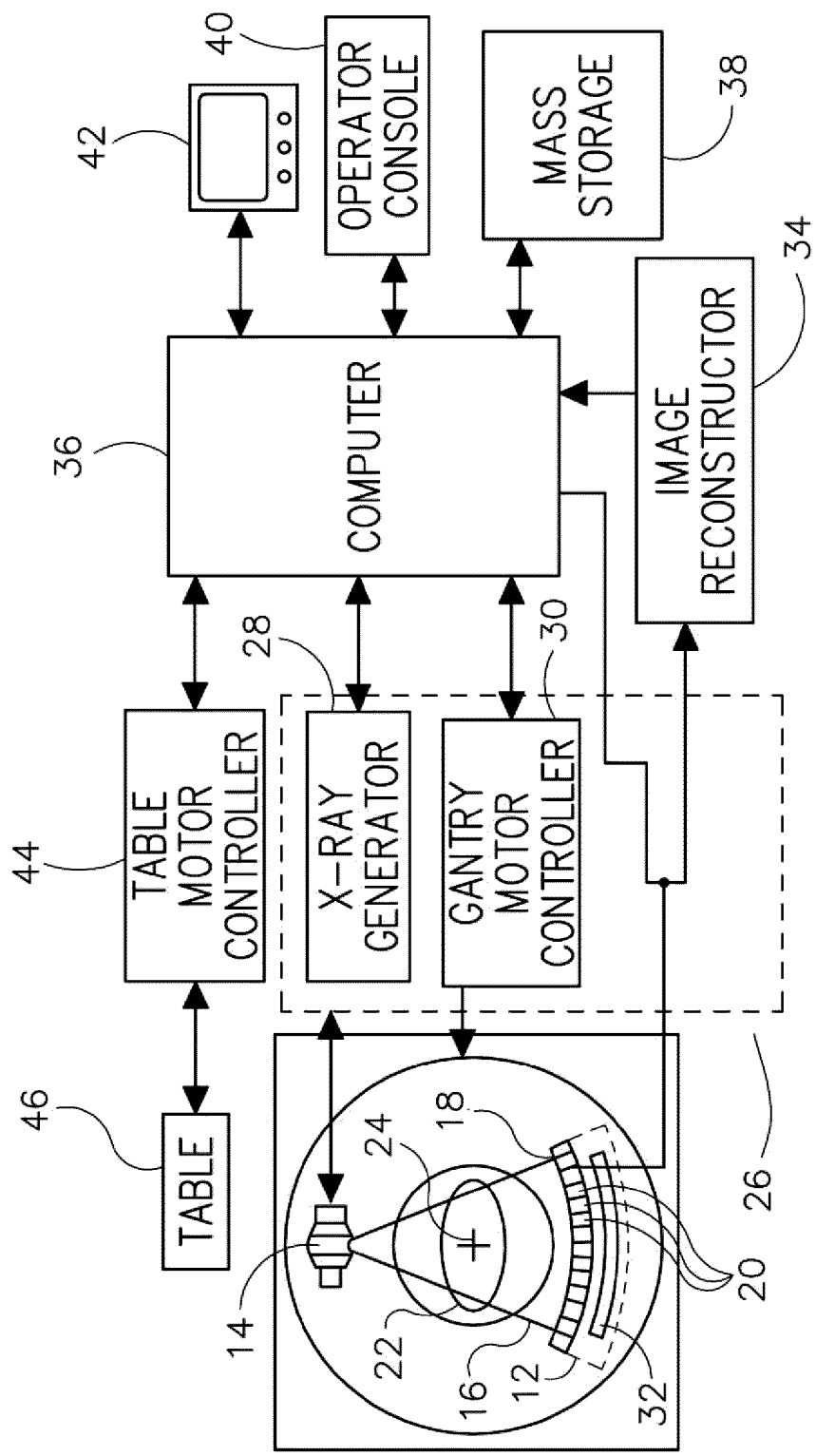
FIG. 2 shows a functional block diagram of the computed tomography imaging system of FIG. 1.
Figure 3:
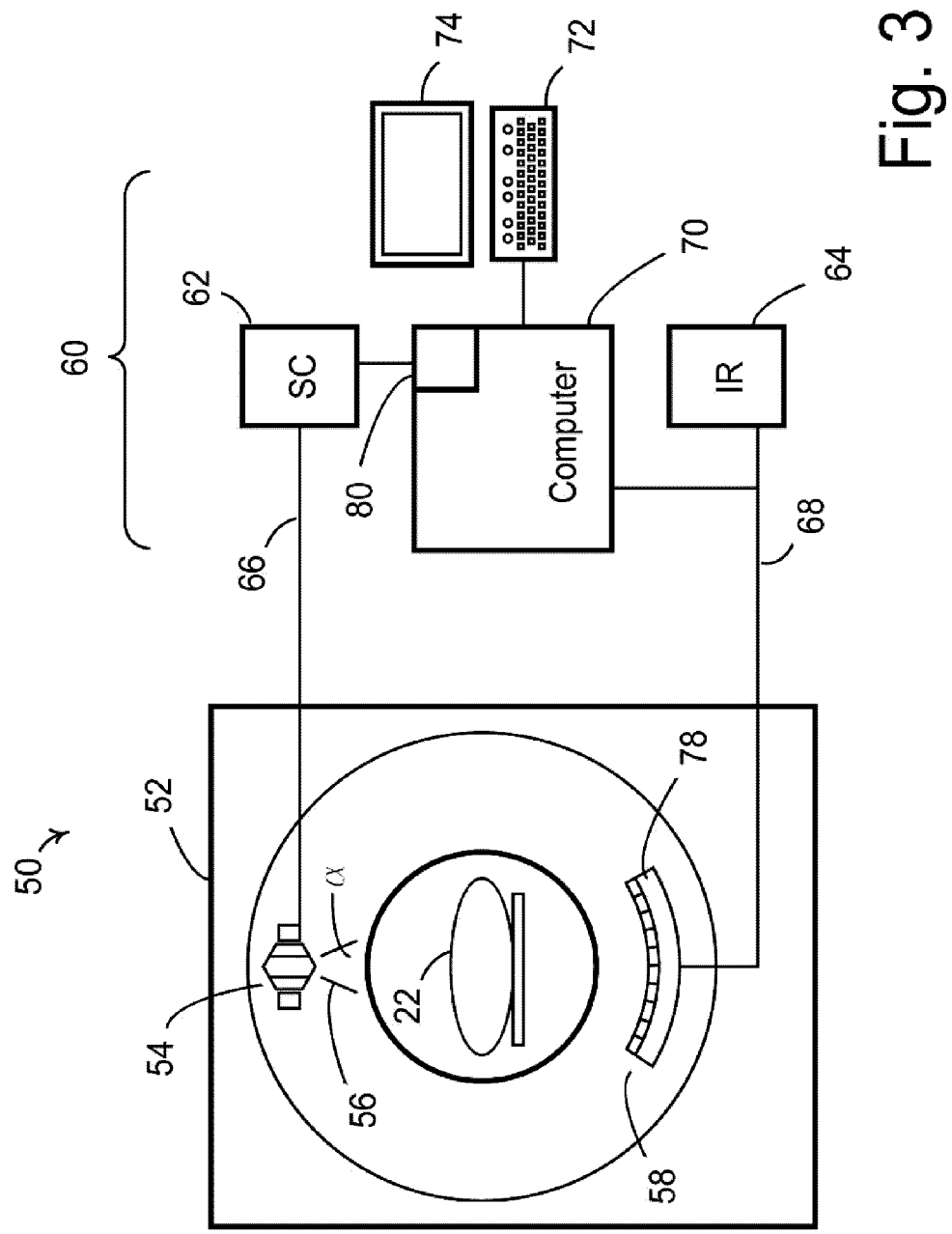
FIG. 3 is diagrammatical illustration of a computed tomography imager comprising a gantry, an x-ray source, and a computed tomography imager control system, in accordance with one exemplary aspect of the present invention.

Referring now to FIG. 3, a CT imager 50 includes a gantry 52 with an x-ray source 54 and a detector assembly 58 mounted inside the gantry 52. The x-ray source 54 operates to project a substantially fan-shaped x-ray beam 56 (defined by a fan angle α) at the detector assembly 58, which is fixed with respect to the x-ray source 54, where the x-ray beam 56 is substantially collimated to lie within an "imaging plane." The angle of the x-ray beam 56 changes with respect to an imaging target, such as the patient 22, as the gantry 52 rotates the x-ray source 54 and the detector assembly 58 in a circumferential path about the imaging target. A series of x-ray attenuation measurements obtained from the detector assembly 58 at a specified angle is referred to as a "view" and a set of views made at different angular orientations during a complete rotation of the x-ray source 54 and the detector assembly 58 is referred to as a "scan slice" of the patient 22. Subsequent "axial" or "helical" scans of the patient 22, through gantry angles of 360°, may be made as the patient 22 is moved longitudinally through the gantry opening 48 (see FIG. 1).

A CT imager control system 60 functions to modulate both kVp and mA in the x-ray source 54 using a computer 70 to execute an x-ray modulation software program 80 configured in accordance with the disclosed method. As can be appreciated by one skilled in the art, the x-ray modulation software program 80 may reside in firmware, or in a removable magnetic or optical storage device (not shown), such as a floppy disk, a CD-ROM, a DVD, or any other digital device. Alternatively, the x-ray modulation software program 80 may be accessible to the computer 70 via a digital network (not shown), such as an Ethernet, for reading instructions and/or data from a remote database. Moreover, as the computer 70 is programmed to perform the functions described herein, the computer 70 may comprise any one or more of a processor, a microcontroller, a microcomputer, a programmable logic controller, an application specific integrated circuit, or any other programmable circuit configured to execute the x-ray modulation software program 80 in accordance with the disclosed method.

The computer 70 directs an x-ray source controller 62 to provide power and timing signals to the x-ray source 54, and to automatically set kVp and mA operating levels over a control line 66. The computer 70 also receives sampled and digitized x-ray data over a signal line 68 from a data acquisition system 78 in the detector assembly 58. An image reconstructor 64 may perform high speed reconstruction from the sampled and digitized x-ray data to provide a cross-sectional image showing inner detail structure of the patient 22 or other imaging target. Reconstructed image data may be sent to the computer 70. The computer 70 may also receive commands and scanning parameter inputs from an operator console 72. A console display 74 enables an operator to observe reconstructed images and other data from the computer 70. The commands and scanning parameters may be used by the computer 70 to provide control signals and information to the data acquisition system 78 and to the x-ray source controller 62.

Figure 4:
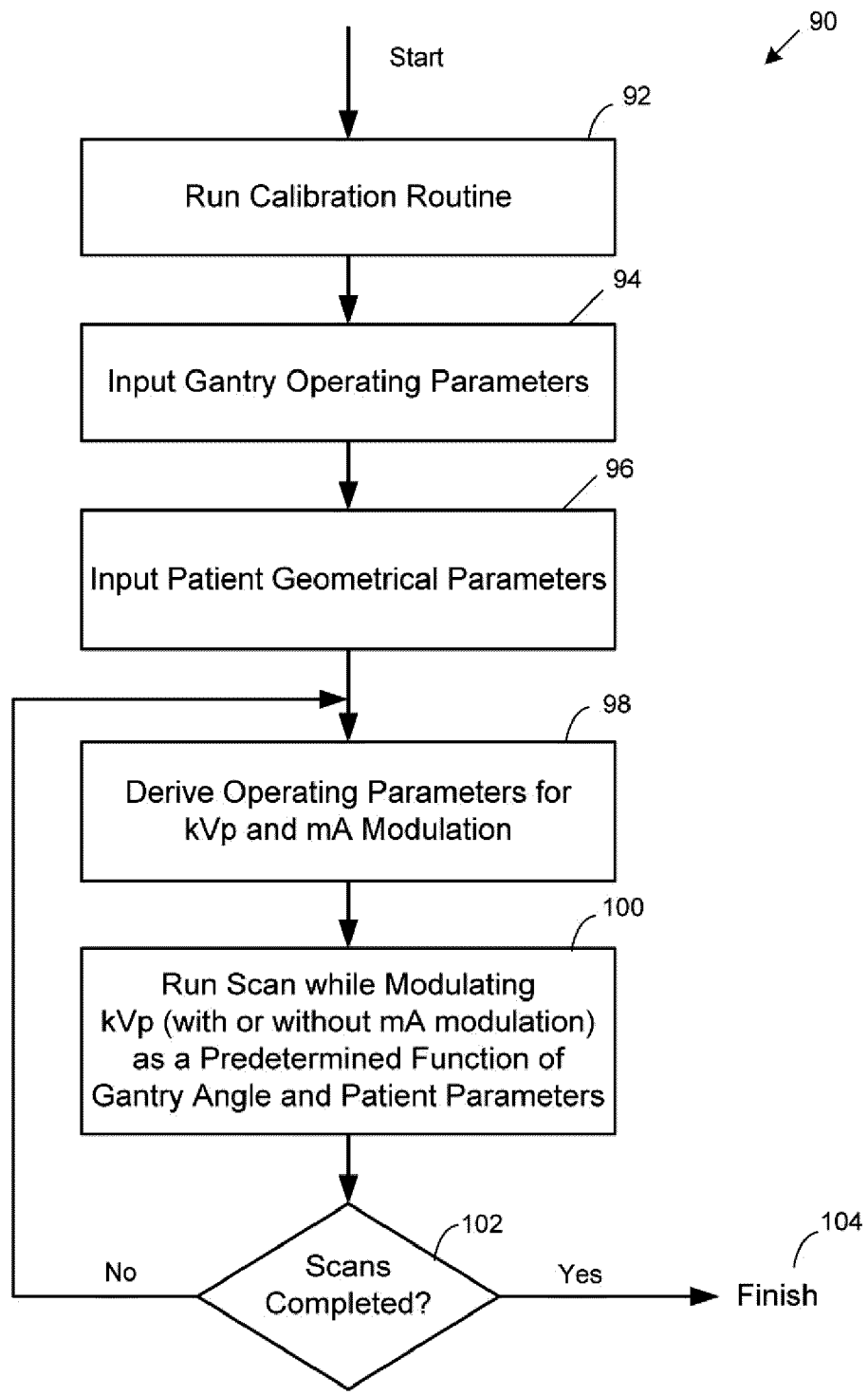
FIG. 4 is flow diagram describing operation of the computed tomography imager of FIG. 3.
Figure 5:
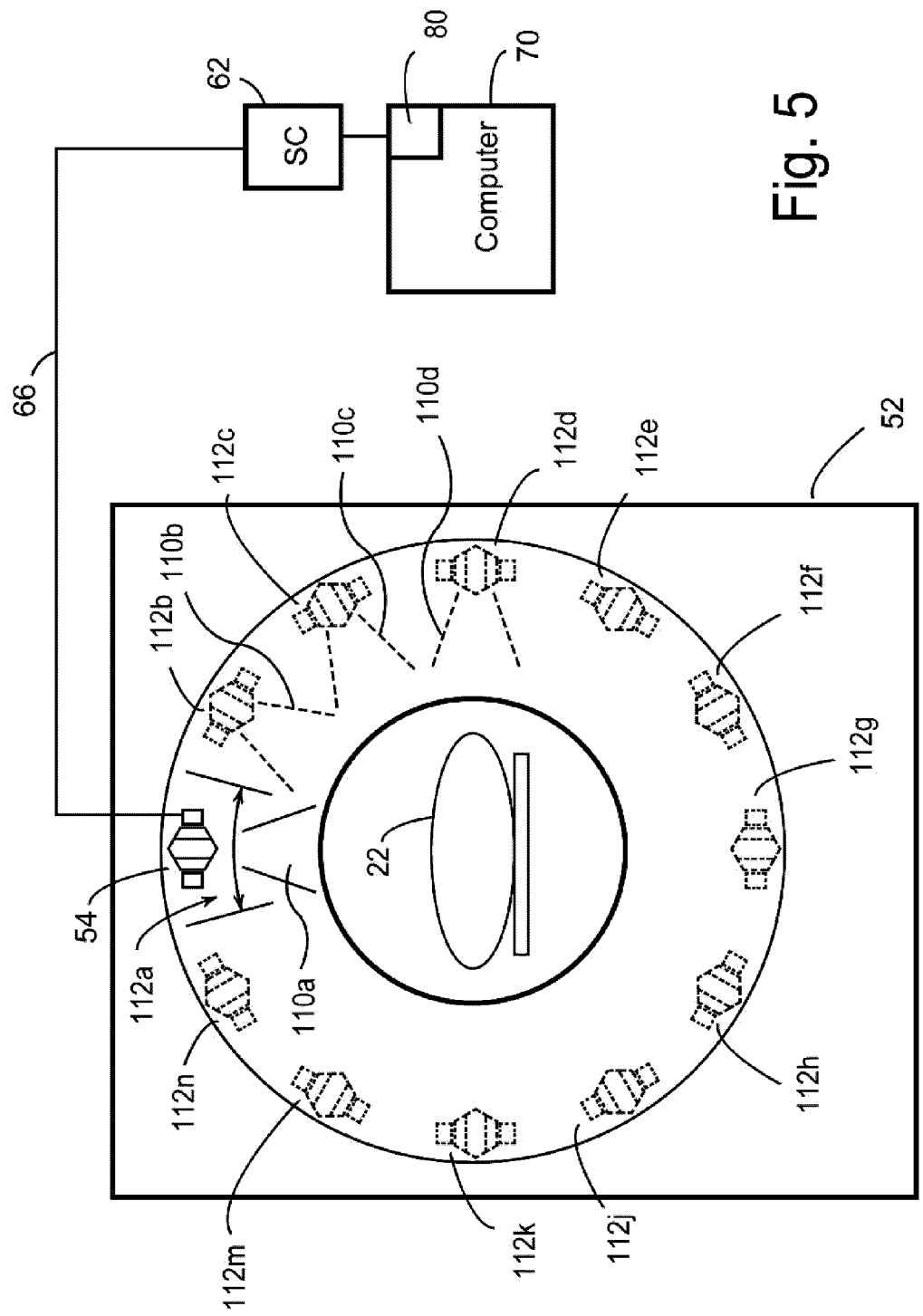
FIG. 5 is more detailed diagrammatical illustration of the computed tomography imager of FIG. 3 showing modulation of x-ray source voltage (kVp) as a function of angular position of the x-ray source.

An exemplary method of controlling patient x-ray radiation exposure by modifying operating kVp while maintaining optimal contrast can be described with reference to a flow diagram 90, in FIG. 4, and a diagrammatical elevation view of the patient 22 being imaged in the gantry 52, in FIG. 5. A calibration routine may be performed, at step 92, to calibration the kVp spectral and air profile, prior to executing a scanning procedure on the patient 22. An exemplary calibration routine suitable for use in the CT imager 50 is described in commonly-assigned U.S. Pat. No. 7,086,780 "Methods for spectrally calibrating CT imaging apparatus detectors," incorporated herein by reference. It can be appreciated that, in a conventional scan, calibration vectors are generated based on the X-ray energy spectra, where there are a limited number of kVp spectra in the system. In the calibration routine of step 92, the spectrum of each view may be captured as a combination of basis spectra. Accordingly, calibration vectors can be derived based on this information. The method of capturing the transiting kVp spectrum as a combination of the basis spectra may be achieved by either a simple interpolation or a more sophisticated calibration process.

Gantry parameters, such as initial position of the x-ray source 54 and a longitudinal scan position, that is, the longitudinal position of the x-ray source 54 emission on the patient 22, may be input to the computer 70, at step 94. Patient parameters, such as height and weight, may also be input to the computer 70, at step 96. This allows for the disclosed method to obtain an optimal signal-to-noise ratio adaptive to patient size. The x-ray modulation software program 80 may use these input parameters to derive operating parameters for kVp modulation, and alternatively, for mA modulation, at step 98. For example, kVp modulation can be: (i) prescribed from the measurement of CT scout images, with x-ray source 54 positions at 12/6 clock and 9/3 clock, (ii) dynamically determined based on the real-time projection data during a scan at various source positions, (iii) based directly on the weight and size of the patient 22, (iv) based on the longitudinal location of a current scan on the patient 22; and (v) based on or dynamically determined from a corresponding mass penetration length requirement. This allows for optimizing the dose and the contrast-to-noise ratio to improve image quality.

It can be appreciated by one skilled in the relevant art that the high voltage output of the x-ray source 54 is kVp configurable. Additionally, the method of obtaining spectral calibration at any kVp may be done with only limited measurements. That is, spectral calibration can be obtained with measurements obtained at four or more kVp values to derive the spectral calibrations for the remaining kVp values. Air calibration data may be obtained for a given kVp based on measurements from a few limited kVp values, for example, from four kVp readings. The projections at a given kVp value may be corrected by air calibration and spectral calibration, using matching calls computed from measurements from a limited number of kVp values. The kVp modulations can be determined dynamically from projection data.

An axial or a helical scan may be run, with an initial modulated x-ray beam 110a irradiating the patient 22 over a first gantry scan angular range 112a, to obtain a scan slice, at step 100. The kVp emission is modulated within each scan slice in accordance with values determined by the x-ray modulation software program 80. For example, the value of kVp may be increased when a longer mass penetration length (e.g., the side-to-side dimension of the patient 22) is presented to the x-ray source 54, and decreased for a shorter mass penetration length (e.g., the front-to-back dimension of the patient 22). It should be understood that the mA value may also be modulated within each scan slice while the kVp operating value is being modulated, as may be specified by the x-ray modulation software program 80.

A first "view" may be thus be obtained at the initial gantry scan angular range 112a, shown here as a thirty degree arc segment generally centered about a 12 o'clock position, or gantry angle, in the gantry 52. As the x-ray source 54 moves along a circumferential path to a second gantry scan angular range 112b, the patient 22 may be then be irradiated with a modulated x-ray beam 110b over the adjacent thirty degree arc segment. The gantry scan may continue to a third angular range 112c, over which the modulated x-ray beam 110 may output a modulated x-ray beam 110c. After the CT imager 50 has scanned across the third angular range 112c, the CT imager 50 may move to a fourth angular range 112d with a modulated x-ray beam 110d generally centered about a 3 o'clock position in the gantry 52. The scan slice is obtained when the x-ray source 54 has returned to the first gantry scan angular range 112a to obtain the next scan slice.

Thus, in an exemplary embodiment, the kVp operating value of the x-ray source 54 may be modified during a scan slice, as a function of gantry angle. That is, kVp and mA are automatically controlled by the x-ray modulation software program 80, as a function of the angular position of the x-ray source 54 with respect to the patient 22, so as to both minimize exposure to the patient and to maintain an optimal contrast in the output image data. As understood in the relevant art, CT scans may be performed at rotational speeds ranging from about 0.3 seconds per rotation to about 1.0 seconds per rotation. The CT imager 50 may acquire about 1000 views per gantry rotation for sufficient angular sampling to provide acceptable resolution in the reconstructed image. For a CT imager operating with these parameters, the longest interval of time for a view is on the order of a millisecond. It can be appreciated by one skilled in the art that a human operator is not capable of manually modifying kVp and mA in the manner described above within the one millisecond scan slice timeframe realized in CT systems.

The x-ray modulation software program 80 may function to modify the kVp settings in accordance with predetermined parameters stored in the x-ray modulation software program 80. The predetermined parameters may comprise values determined empirically, or derived by analysis, for example. Exemplary kVp values for an adult patient lying inside the gantry are provided in Table 1. As can be seen, the relatively low x-ray source voltage of 80 kVp, provided in the angular ranges 112a and 112g, is used for imaging through a smaller dimension of the patient 22 (e.g., the chest cavity) while the relatively large x-ray source voltage of 140 kVp, provided in the angular ranges 112d and 112k, is used for imaging though a larger dimension of the patient 22 (e.g., the shoulders).

In an exemplary embodiment, each kVp value in Table 1 is an optimized value, derived by specifying a value great enough to image the target path length, so as to provide to the data acquisition system 78 a signal having a high signal-to-noise ratio, and keeping the value small enough to minimize the radiation dosage delivered to the patient 22. As can be appreciated by one skilled in the art, the disclosed method of modifying kVp during a scan slice can provide quality image data while reducing patient radiation exposure. In comparison, a conventional scanning procedure may specify a constant kVp value for the entire scan slice, where the constant kVp is selected to reduce patient exposure, but where the constant kVp may be inadequate to provide for a long mass penetration length.

As can be appreciated by one skilled in the art, the present invention may be practiced with any voltage settings or modulation functions preselected for execution by and stored in the x-ray modulation software program 80. As described above, the value of the kVp operating value may also be modified dynamically, that is, determined from real-time projection data obtained at various gantry angle positions of the x-ray source 54 during a scan. Alternatively, the value of the kVp operating value may be modified as a function of the weight and size of the patient 22, and/or as a function of the longitudinal location of the current scan on the patient 22. If the series of scans have been completed, at decision block 102, the scanning procedure may be finished, at step 104. Otherwise, the scanning procedure may be continued by repeating steps 98 and 100.

TABLE 1

| X-Ray Source Angular Range | X-Ray Source Voltage |
|---|---|
| 112a, 112g | 80 kVp |
| 112b, 112f, 112h, 112n | 100 kVp |
| 112c, 112e, 112j, 112m | 120 kVp |
| 112d, 112k | 140 kVp |

As shown in Table 1, the kVp operating value setting on the x-ray source 54 varies from about 80 kVp to about 140 kVp in the various thirty-degree angular ranges. In an exemplary embodiment, the modulated voltage level is essentially constant within each angular range and undergoes an essentially step increase or decrease at the next angular range. In an alternative exemplary embodiment, the modulated voltage level may vary within each angular range such that the voltage transition is relatively smooth from one angular range to the next. That is, the kVp modulation may be smooth in time, or with angular gantry position, such that no high frequency modulation in time (i.e., fast up and down in kVp value) is needed, and to minimize spectral related image artifacts. The kVp operating value may be fixed at a constant value during each scan if that is the optimized selection, and the kVp operating value may be modulated according to the x-ray penetration length at each projection angle, depending on the patient geometry.

In an alternative exemplary embodiment, kVp modulation can be performed over only a portion of the total possible rotational scanning range of the x-ray source 54. In particular, the view angle coverage (i.e., the angle over which the x-ray source 54 rotates), or the angle for performing the kVp modulation, can be as small as (180°+α), that is, half the rotational range of the gantry 52 plus the fan angle (α), shown in FIG. 3. This minimum view angle coverage is large enough to allow for reconstruction of a CT image.

For a geometrically symmetric object or patient, the kVp operating value may be kept constant over most or all the angular ranges. In an exemplary embodiment, the disclosed method provides for an automatic kVp/mA selection at a continuous kVp/mA range, such that the combination of specified kVp and mA provides the optimal contrast-to-noise ratio under a specified patient exposure. As can be appreciated by one skilled in the relevant art, a conventional medical CT scanning system, which allows the operator to select from only four or five discrete kVp operating values, does not provide for a method to optimize the contrast-to-noise ratio.

Figure 6:
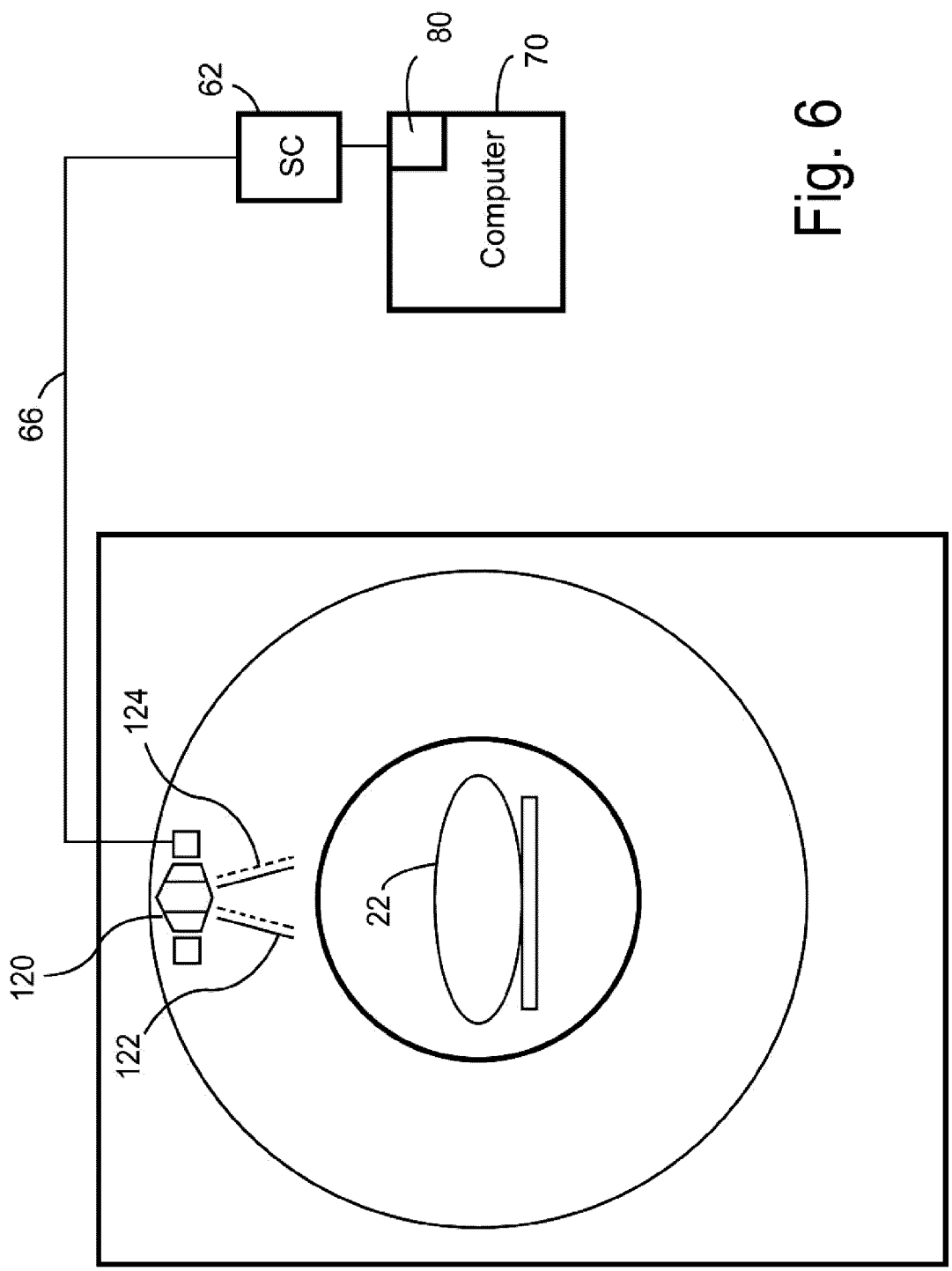
FIG. 6 is an alternative embodiment of the computed tomography imager of FIG. 3 comprising a dual x-ray source.

In an alternative embodiment, shown in FIG. 6, a dual x-ray source 120 may be used to generate two fan-shaped x-ray beams 122 and 124 having different kVp operating values. In an exemplary embodiment, the x-ray beam 122 may operate at an 80 kVp value, and the x-ray beam 124 may operate at a 140 kVp value. The x-ray source controller 62 and the x-ray modulation software program 80 function to provide fast dual kVp switching, where the kVp operating values may be modulated within two independent ranges of fixed and distinct kVp values, herein denoted as a first kVp operating range and a second kVp operating range.

Accordingly, the radiation dose provided to the patient 22, or other imaging target, requires optimizing the two kVp operating ranges as a function of mass penetration length. In an exemplary embodiment, the 80 kVp operating value may be slowly changed to a 100 kVp value as mass penetration length requirement increases with gantry rotation, and the 140 kVp operating value may be increased to about 160 kVp. The first kVp operating range settings and the second kVp operating range settings can be pre-computed from a scout scan, or may be dynamically determined based on real-time scan data, to provided optimal scanner parameters for the patient 22 during the dual kVp scan.

While the present invention is described with reference to various exemplary embodiments, it will be understood by those skilled in the art that various changes may be made and equivalence may be substituted for elements thereof without departing from the scope of the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. In particular, certain modifications may be made to the teachings of the invention to adapt to a particular situation without departing from the scope thereof. Therefore, it is intended that the invention not be limited to the embodiments disclosed above for carrying out this invention, but that the invention include all embodiments falling with the scope of the intended claims.

What is claimed is:

1. A computed tomography imager suitable for obtaining scan slices of an imaging target, said imager comprising:
   an x-ray source disposed in a gantry;
   a detector assembly for receiving an x-ray emission from said x-ray source, said x-ray source and said detector assembly rotatable about the imaging target;
   an imager control system for selectively modulating a kVp operating value in said x-ray source during a scan slice in accordance with an x-ray modulation software program; and
   a computer for receiving data from said detector assembly, and for providing control signals to said imager control system by executing said x-ray modulation software program for at least a portion of a total possible rotational scanning range of said x-ray source,
   wherein said x-ray emission comprises a substantially fan shape defined by a fan angle, and said x-ray modulation software program functions to modulate said kVp operating value over a scanning view angle of approximately 180° plus said fan angle.

2. The computed tomography imager of claim 1, wherein said x-ray modulation software program further functions to modulate an mA operating value as a function of at least one of patient parameter and gantry angle.

3. The computed tomography imager of claim 1, wherein said x-ray source comprises either a dual x-ray source producing a first fan-shaped x-ray beam operating at a first kVp value and a second fan-shaped x-ray beam operating at a second kVp value, or a single source rapidly switching between said first kVp value and said second kVp value.

4. The computed tomography imager of claim 3, wherein said first kVp value is approximately 80 kVp and said second kVp value is approximately 140 kVp.

5. The computed tomography imager of claim 3, wherein said imager control system functions to modulate said first kVp operating value independently of modulating said second kVp operating value.

6. The computed tomography imager of claim 1, wherein said imager control system functions to increase said kVp operating value in response to an increased mass penetration length requirement.

7. A method for controlling patient exposure to radiation emitted in a scanning system gantry, said method comprising the steps of:
   obtaining predetermined operating parameters as a function of gantry angle for modulating a kVp operating value for a radiation source during a scan; and
   modulating said kVp operating value for said radiation source during at least a portion of a scan slice in accordance with said operating parameters,
   wherein said operating parameters comprise at least one of a patient height, a patient weight, a gantry angle, and a longitudinal scan position.

8. The method of claim 7, further comprising the step of modulating an mA operating value for said radiation source during said step of modulating said kVp operating value.

9. The method of claim 7, wherein said kVp operating value comprises a value of approximately 80 kVp to 160 kVp.

10. The method of claim 7, wherein said step of modulating said kVp operating value comprises the step of increasing said kVp operating value as a corresponding mass penetration length requirement increases.

11. A method for controlling patient exposure to radiation in a computed tomography scanning system, said method comprising the steps of:
    irradiating the patient with an x-ray source controlled by an imager control system, said imager control system functioning to selectively modulate a kVp operating value for said x-ray source in accordance with an x-ray modulation software program; and
    modulating said kVp operating value during each scan slice of a computed tomography scan,
    wherein said kVp operating value remains essentially constant over a predefined angular range of said scan slice for said x-ray source.

12. The method of claim 11, wherein said x-ray source comprises either of a single x-ray source rapidly switching between a first kVp and a second kVp or a dual x-ray source for generating two x-ray beams, each of said two x-ray beams having a different kVp operating value.

13. The method of claim 12, wherein said first kVp value is approximately 80 kVp and said second kVp value is approximately 140 kVp.

14. The method of claim 11, wherein said step of modulating said kVp operating value comprises a step of basing said kVp operating value modulation on measurements obtained from computed tomography scout imaging.

15. The method of claim 11, wherein said step of modulating said kVp operating value comprises a step of dynamically modifying said modulation based on real-time projection data obtained during computed tomography scans performed at a plurality of x-ray source positions.

16. The method of claim 11, wherein said step of modulating said kVp operating value comprises a step of basing said kVp operating value modulation on patient weight and size parameters.

* * * * *